United States Patent [19]

Finkelstein et al.

[11] 4,229,530
[45] Oct. 21, 1980

[54] METHODS AND MEDIA FOR RAPID DETECTION OF PATHOGENIC NEISSERIA

[75] Inventors: Richard A. Finkelstein, Dallas, Tex.; Shelley M. Payne, Albany, Calif.

[73] Assignee: Board of Regents, University of Texas System, Austin, Tex.

[21] Appl. No.: 937,881

[22] Filed: Aug. 29, 1978

[51] Int. Cl.$^3$ .............................................. C12Q 1/12
[52] U.S. Cl. ..................................... 435/37; 435/244; 435/253; 435/871
[58] Field of Search ................ 195/103.5 M, 103.5 R, 195/99, 100, 101, 102, 103; 435/37, 244, 253, 871

[56] References Cited

U.S. PATENT DOCUMENTS

| Re. 24642 | 4/1959 | London et al. | 424/180 |
|---|---|---|---|
| 2,820,740 | 1/1958 | London et al. | 424/180 |
| 2,885,393 | 5/1959 | Herb | 424/180 |
| 3,936,355 | 2/1976 | Lawson | 195/100 |
| 4,039,387 | 8/1977 | Simpson et al. | 195/103.5 M X |

OTHER PUBLICATIONS

Douglas S. Kellogg et al., Neisseria gonorrhoeae, Journal of Bacteriology, vol. 96, No. 3 (Sep.) pp. 596–605, 1968.
The Merck Index, 9th Edition, 2906, p. 387, 1976.
Shelley M. Payne et al., Pathogenesis and Immunology of Experimental Gonococcal Infection, Infection & Immunity, vol. 12, pp. 1313–1318, 1975.
Julius Grant, Hackh's Chemical Dictionary, p. 206, 1969.

*Primary Examiner*—Robert J. Warden
*Attorney, Agent, or Firm*—Arnold, White & Durkee

[57] ABSTRACT

A microbial growth medium for the isolation and rapid detection of *Neisseria gonorrhoeae* and *Neisseria meningitidis*, having incorporated therein an iron-dextran complex in a quantity sufficient to stimulate maximum colony growth.

12 Claims, No Drawings

METHODS AND MEDIA FOR RAPID DETECTION OF PATHOGENIC NEISSERIA

BACKGROUND OF THE INVENTION

1. Field

This invention relates generally to microbial growth media and specifically to an improved isolation medium for the rapid detection of pathogenic Neisseria, *Neisseria gonorrhoeae* and *Neisseria meningitidis*, the causative agents of gonnorrhea and cerebrospinal meningitis diseases.

2. Prior Art

Diagnosis of infection by pathogenic Neisseria requires the use of a suitable culture medium, one which will permit the in vitro growth of the pathogenic Neisseria and inhibit the growth of other bacteria. Typically, in the prior art, a specimen is inoculated onto the surface of a suitable medium and incubated under suitable conditions for a period of time up to 48 hours. Pathogenic Neisseria which are present in the specimen will grow and form colonies which can then be detected by visual inspection.

Various types of culture media have been utilized in the prior art. For example, Simpson et al, U.S. Pat. No. 4,039,387, relates to a growth medium for distinguishing between *Neisseria gonorrhoeae* and *Neisseria meningitidis*.

The particular medium most widely used in the art at the time of this application is known as the Thayer-Martin medium. This medium was disclosed in 1966 by Messrs. Thayer and Martin in Public Health Rep. 81: 559–562. It has been observed that the Thayer-Martin medium is less than 100 percent effective in isolating *N. gonorrhoeae*, isolation rates ranging from about 40 percent to about 90 percent. This means that only about 40 to 90 percent of the specimens known to contain the bacteria will show growth. In a clinical situation, this means that from 10 percent to 50 percent of all individuals infected with the disease will remain undetected after observation of the first culture.

In view of the increasing incidence of the disease to epidemic proportions and further in view of the very large numbers of cases, both reported and unreported, the difference in detection rates is very important. It is perhaps even more important with respect to the other pathogenic Neisseria, *N. meningitidis*, since this bacteria causes a potentially fatal disease the prompt and accurate detection of which is, in many cases, critical.

It is known in the prior art to use cations such as ferric ions or aluminum ions in a medium for the detection of pathogenic Neisseria in order to increase the growth of the bacteria. For example, in U.S. Pat. No. 3,936,355, Lawson discloses the use of ferric nitrate in a culture medium for supporting the growth of certain types of microorganisms, including *Neisseria gonorrhoeae* and *Neisseria meningitidis*. The standard practice in the prior art has been to add iron to the culture medium in the form of ferric nitrate.

Kellogg et al investigated *Neisseria gonorrhoeae* and in their paper, *Neisseria Gonorrhoeae, J. Bacteriology*, September 1968, 596, identified four distinct colonial forms of gonococcus, T1, T2, T3 and T4. The former two types were shown to be virulent to man and the latter two to be relatively avirulent. At page 600, Kellogg et al observed the importance of including ferric ions in the culture medium to promote growth of the bacteria. Kellogg et al point out that the types of anions accompanying the ferric ions had no effect on the results, and that while glucose alone was ineffective to promote increased growth, use of glucose with ferric ions produced "an additive effect". In FIG. 4, at Page 600 of their paper, Kellogg et al plotted the growth stimulation in colony diameter with the inclusion of ferric ions, with the inclusion of glucose, and with the inclusion of a mixture of glucose and ferric ions wherein the ratio of glucose to ferric ions was 1.0. These results indicate that the increase in colony diameter in the medium is only slightly greater when a glucose/ferric combination is utilized compared to the use of ferric ions alone. Further, Kellogg et al point out at Page 600 of their paper that "a ratio of glucose to ferric ions of less than one depressed the colony size to a level intermediate between that obtained with either additive alone."

In their paper entitled "Pathogenesis and Immunology of Experimental Gonococcal Infection: Role of Iron in Virulence," (1975, *Infect. Immun.* 12: 1313–1318), applicants disclosed the creation of an experimental animal model, chicken embryos, with findings that the colonial types previously identified as virulent (T1 and T2) killed the animals, and that the forms identified as relatively nonvirulent (T3 and T4) did not. Applicants further disclosed in that paper that the virulence of the T3 and T4 types to chicken embryos is enhanced by adding iron in various forms, including in the form of an iron-dextran complex (specifically, Imferon).

The present invention of applicants was first disclosed in their paper entitled "Imferon Agar: Improved Medium for Isolation of Pathogenic Neisseria," *J. Clinical Microbiology*, Volume 6, Number 3, September 1977, pp. 293–297.

It has been estimated that there are some three to four million cases of gonorrhea each year in the United States, most of which go unreported. Improvement in the rate of detection of gonorrhea from a first culture would represent a significant advancement in the art. Such improvement can be obtained by devising a method and composition for effectively increasing the colony size of the bacteria *Neisseria gonorrhoeae* so that the presence of the bacteria may be readily observed within a short period of time. Similar advantages would also result if an improved medium could be developed for the detection of the other pathogenic Neisseria, *Neisseria meningitidis*.

This invention seeks to develop such methods and such a medium to improve the speed and rate of isolation of *Neisseria gonorrhoeae* and *Neisseria Meningitidis*, so that their colonies are much larger in size and will appear after a much shorter incubation period.

SUMMARY OF THE INVENTION

This invention provides growth media for the rapid detection of pathogenic Neisseria, which incorporate an iron-dextran complex as the source of iron in standard gonococcal and meningicoccal-specific culture media.

Further, this invention provides methods for the rapid detection of pathogenic Neisseria, which include the step of incorporating into a gonococcal and meningicoccal-specific medium as the source of iron, an iron-dextran complex.

DETAILED DESCRIPTION OF PREFERRED EMBODIMENTS

*Neisseria gonorrhoeae* and *Neisseria meningitidis* are the two pathogenic members of the Neisseria family. In accordance with the preferred embodiments of this invention, improved media and methods for the isolation and rapid detection of these pathogenic Neisseria are provided.

According to the methods of this invention, a standard gonococcal and meningicoccal-specific medium is provided, which medium will stimulate the growth of the bacteria as measured by increased colony diameter. A suitable standard gonococcal and meningicoccal-specific medium is that commonly used in the art known as the GC medium base which may be obtained from Difco Laboratories, Detroit, Mich. GC base is a standard culture medium which is specifically designed for growing gonococcal and meinigicoccal bacteria.

To this standard medium is added an operable amount of an iron-dextran complex. An operable amount of iron-dextran complex is that sufficient to give a final concentration of at least about 5 micrograms per milliliter, and preferably approximately 20 micrograms of iron per milliliter of medium. Applicants have found that an operable amount is at least about 0.01 percent by volume of the iron-dextran complex.

An example of the iron-dextran composition which is useful in connection with the invention is the product marketed by Richardson-Merrill Inc. under the trademark Imferon, which product is available, for example, from Lakeside Laboratories, Inc., Milwaukee, Wis. Where the product Imferon is utilized, the amount of Imferon preferred for use by applicants is approximately 0.04 volume percent.

To the standard base containing the iron-dextran complex may be added a nutritional supplement such as the so-called Kellogg supplement which is also commonly available in the industry, in the amount of approximately 1 percent by volume. A selective antibiotic is also preferably added to the medium to prevent the growth of other bacteria while still permitting the growth of the pathogenic Neisseria. Such an antibiotic is vancomycin-colistin-nystatin (V-C-N).

The culture medium as described above is mixed in agar, which is a gelatinous colloidal extractive of a red alga commonly used in culture media.

To the iron-dextran containing medium thus provided, and further in accordance with the methods of this invention, a suitable amount of said medium, e.g. about 25 milliliters, is retained in a container such as a plastic Petri dish and inoculated with a culture containing a pathogenic Neisseria. This may be done in any suitable manner well-known in the art, for example by the streaked cotton swab method. The plates are then incubated, preferably at 37° C. in 10 percent carbon dioxide for a period of time of at least about 20 hours.

Following incubation, the growth of bacteria is observed to ascertain the presence of pathogenic Neisseria.

Applicants have found from both laboratory and clinical experimentation that the methods and media disclosed above yield superior results when compared with the methods and media of the prior art. Some of the experiments of applicants are reported in the examples which follow.

In Examples I through IV, applicants demonstrate the effect of increasing amounts of Imferon on colony growth of pathogenic Neisseria.

EXAMPLE I

A control medium was prepared as follows:

A GC medium base from Difco Laboratories of Detroit, Mich., was provided. To this GC medium base one percent of a Kellogg supplement [which is described at *J. Am. Vener. Dis. Assoc.* 1:14–19] was added omitting the ferric nitrate, and one percent of the selective antibiotic vancomycin, colistin and nystatin (V-C-N), obtained from Baltimore Biological Laboratory of Cockeysville, Md., was also included in the medium.

About 25 milliliters of the media thus prepared were placed in a plastic Petri dish.

To the medium thus prepared, three samples of pathogenic Neisseria were added, the first being *Neisseria gonorrhoeae*, type T1, the second being *Neisseria gonorrhoeae*, type T3, and the third being *Neisseria meningitidis*. The samples of *Neisseria gonorrhoeae* were strain F62 provided by D. S. Kellogg, Jr., Center for Disease Control, Atlanta, Ga. The *Neisseria meningitidis* was strain B-11 obtained from H. Schneider, Walter Reed Army Institute for Research, Washington, D.C.

Equal volume droplets of dilutions of suspensions of gonococci and meningicocci were plated by the streaked cotton swab technique on the culture media media being compared. Plates were incubated at 37° C. in 10 percent carbon dioxide. After 20 hours of incubation, the numbers of colonies and their average size were determined by using a dissecting microscope fitted with an optical reticle. The results of these tests are reported in the first column of Table 1.

EXAMPLE II

Example I was repeated, except that 4 micrograms of iron in the form of Imferon were added to the control medium.

The three bacteria mentioned above were added in the same manner, and incubated under the same conditions and for the same period of time.

The results of these tests are reported in the second column of Table 1, and indicate significant increases in colony size for all three bacteria tested.

EXAMPLE III

Example I was repeated, except that 8 micrograms per milliliter of iron in the form of Imferon were added.

The three bacteria of Example I were tested in the same manner as indicated in that example.

The results of these tests are reported in the third column of Table 1, and show that even greater increases in colony size were obtained in all instances.

EXAMPLE IV

Example I was repeated, except that 20 micrograms per milliliter of iron in the form of Imferon were added to the culture medium.

The three bacteria of Example I were added and incubated in the same manner as specified in that example.

The results of these tests are shown in Column 4 of Table 1, and indicate significant increases in colony size for all three bacteria. The total increase in colony size in Example IV, as compared to Example I, was more than fivefold in the case of *Neisseria meningitidis* B-11, was nearly fourfold in the case of *Neisseria gonorrhoeae* T3, and was some threefold in the case of *Neisseria gonorrhoeae* T1.

TABLE 1

Amount of iron in the form of Imferon in medium of Examples I-IV vs. average colony diameter in millimeters

|  | 0 | 4 μg | 8 μg | 20 μg |
|---|---|---|---|---|
| N. meningitidis B-11 | 6 | 11 | 16 | 31 |
| N. gonorrhoeae T3 | 4 | 6 | 8 | 15 |
| N. gonorrhoeae T1 | 2 | 3 | 4 | 6 |
|  | Ex. I | Ex. II | Ex. III | Ex. IV |

Applicants also conducted tests to compare the change in colony size of *Neisseria meningitidis* B-11, and *Neisseria gonorrhoeae* F62 T1 and T3, between growth media containing various concentrations of Imferon with various other types of media utilized in the prior art. The various media used in these experiments are described below in Examples V through X, with the results of the tests on these media described thereafter.

EXAMPLE V

A culture medium was prepared consisting of a GC medium base plus 1 percent Kellogg supplement.

EXAMPLE VI

A medium comprising GC medium plus 1 percent IsoVitalX, which was obtained from Baltimore Biological Laboratory of Cockeysville, Md., was prepared.

EXAMPLE VII

A Thayer-Martin medium was prepared consisting of GC medium base, 1 percent hemoglobin, and 1 percent IsoVitalX.

EXAMPLE VIII

A medium identical to that used in Example II was prepared.

EXAMPLE IX

A medium identical to that used in Example III was prepared.

EXAMPLE X

A medium identical to that used in Example IV was prepared.

To each of the media prepared in Examples V through X, an identical amount of V-C-N was added.

Each of the media of Examples V through X was simultaneously inoculated with Neisseria meningitidis B-11 in the manner specified in Example I, and allowed to incubate under the conditions and for the time specified in that example.

The results of these tests are shown in FIG. 2 of our article entitled "Imferon Agar: Improved Medium for Isolation of Pathogenic Neisseria," published in the *Journal of Clinical Microbiology*, Volume 6, Number 3, at Page 295, September, 1977.

The results indicate that the colony size for Examples VIII, IX and X were significantly larger than those of Examples V, VI and VII, with the size of the colonies in Example X being significantly larger than those in Example IX, and the size of the colonies in Example IX being significantly larger than those in Example VIII.

Media prepared in accordance with Examples V through X were also inoculated with *Neisseria gonorrhoeae* F62 T1 and T3, and incubated under the same conditions and for the same time as indicated in Example I. The results of these tests are shown in FIG. 3, at Page 296 of the above-mentioned article in the *Journal of Clinical Microbiology*. These tests also demonstrated the improved results obtained with the addition of Imferon.

Applicants also compared their results obtained by the use of Imferon with the use of corresponding amounts of ferric nitrate. The results of these experiments are reported in Examples XI and XII below.

EXAMPLE XI

A medium identical to that of Example I was prepared and separated into four parts. To the second part, 5 micrograms of iron in the form of Imferon were added; to the third part, 10 micrograms of iron in the form of Imferon were added; to the fourth part, 20 micrograms of iron in the form of Imferon were added.

In the manner of Example I, a sample of *Neisseria gonorrhoeae* F62 T1 was added to each sample and incubated in the manner specified in Example I.

The results are reported in the second horizontal column of Table 2, and show that a consistent increase in average colony diameter was realized with the increasing concentration of Imferon.

EXAMPLE XII

A medium was prepared in the manner of Example I. The medium was separated into four equal parts, and to the second part, 5 micrograms of iron in the form of ferric nitrate were added; to the third part, 10 micrograms of iron in the form of ferric nitrate were added; to the fourth part, 20 micrograms of iron in the form of ferric nitrate were added.

In the manner of Example I, equal portions of *Neisseria gonorrhoeae* F62 T1 were inoculated into each of the four samples. After incubation for the period and in the manner suggested by Example I, the average colony size in each of the samples was measured. The results are reported in the second horizontal column of Table 2. The results indicate that, while colony size increased significantly with small concentrations of ferric nitrate, increasing the concentration of ferric nitrate beyond 5 micrograms of iron per milliliter did not result in further increase in colony size. In fact, maximum colony size was realized at 5 micrograms of iron in the form of ferric nitrate.

TABLE 2

Amount of added iron vs. average colony diameter in millimeters

|  | 0 | 5 μg | 10 μg | 20 μg |
|---|---|---|---|---|
| Imferon Ex. XI | 2.2 | 2.9 | 4.2 | 6 |
| ferric nitrate Ex. XII | 2.2 | 4.1 | 3.9 | 3.9 |

Further laboratory experiments were performed utilizing various combinations of ferric nitrate and dextrans T10, T70 and T500. The dextrans alone were found to be somewhat stimulatory for gonococci and meningicocci, and in combination with ferric nitrate, colony sizes approached those obtained with Imferon. However, the use of Imferon rather than a combination of iron and dextran was preferable since results were more consistent and predictable with Imferon.

Applicants also performed clinical tests, the results of which are reported in Example XIII below.

EXAMPLE XIII

In a clinical test performed from subjects attending the Dallas Public Health Department Venereal Disease Clinic, a total of 406 cultures were taken from 389 patients, comprising 151 females and 238 males. The 406 cultures were inoculated in a Imferon agar media prepared in accordance with Example IV, and in a Thayer-Martin medium prepared in accordance with Example VII.

Incubation was in the manner indicated in Example I, except that the plates were read after overnight incubation (16 to 24 hours) in the case of the Imferon medium, and after 40 to 48 hours in the case of the Thayer-Martin medium.

The results of these clinical tests indicated that 182 positive cultures were detected within 24 hours with Imferon agar, and no additional positive cultures resulted when the Imferon agar was incubated for an additional 24 hours.

On the other hand, only 164 positive tests were detected with Thayer-Martin medium despite an additional 24 hours of incubation. The results of this test are reported more fully at Pages 294–295 of the article in *Journal of Clinical Microbiology* mentioned above.

The results of these tests, both laboratory and clinical, confirm the ability of a growth medium which includes an iron-dextran complex to enhance the growth and to provide for more rapid identification of pathogenic Neisseria. Colonies appear readily visible after overnight incubation of *Neisseria gonorrhoeae* even when the inocula are small, and further incubation does not result in any increase in the number of positive cultures. In experiments by applicants, isolation rates were significantly higher, especially in clinical trails. Based on these observations, a culture medium including an iron-dextran complex, and specifically Imferon agar, represents a significant improvement over previously described and widely used methods and media for the isolation of pathogenic Neisseria.

While the invention has been described in terms of preferred embodiments constituting the best mode known to the applicants at the time of this application, various changes may be made in the invention without departing from the scope thereof, which is defined by the following claims:

What is claimed is:

1. A medium for enhancing the growth and rapid detection of pathogenic Neisseria, which includes at least about 5 micrograms of iron in the form of an iron-dextran complex.

2. A medium in accordance with claim 1, wherein the amount of said iron is at least approximately 20 micrograms.

3. A medium in accordance with claim 1, wherein said iron-dextran complex is Imferon.

4. A medium for enhancing the growth and rapid detection of pathogenic Neisseria, including GC medium, approximately 1 percent Kellogg supplement, and an operable amount of a suitable iron-dextran complex capable of enhancing the growth of pathogenic Neisseria.

5. A medium in accordance with claim 4, wherein said iron-dextran complex is Imferon.

6. A medium in accordance with claim 5, wherein the amount of said iron-dextran complex is approximately 0.04 percent by volume.

7. A method for the rapid detection of *Neisseria gonorrhoeae*, comprising providing a gonococcal-specific medium, adding to said medium at least about 0.01 percent by volume of an iron-dextran complex, inoculating said medium with a culture containing *Neisseria gonorrhoeae*, incubating said bacteria in said medium, and observing the growth of the bacteria after at least about 20 hours.

8. A method for the rapid detection of *Neisseria gonorrhoeae*, comprising providing a gonococcal-specific medium, adding to said medium at least about 0.01 percent by volume of Imferon, inoculating said medium with a culture containing *Neisseria gonorrhoeae*, incubating said bacteria in said medium, and observing the growth of the bacteria after at least about 20 hours.

9. A method for the rapid detection of *Neisseria meningitidis*, comprising providing a meningococcic-specific medium, adding to said medium at least about 0.01 percent by volume of an iron-dextran complex, inoculating said medium with a culture containing *Neisseria meningitidis*, incubating said bacteria in said medium, and observing the growth of the bacteria after at least about 20 hours.

10. A method for the rapid detection of *Neisseria meningitidis*, comprising providing a meningococci-specific medium, adding to said medium at least about 0.01 percent by volume of Imferon, inoculating said medium with a culture containing *Neisseria miningitidis*, incubating said bacteria in said medium, and observing the growth of the bacteria after at least about 20 hours.

11. A method for the rapid detection of *Neisseria gonorrhoeae*, comprising providing a gonococcal-specific medium, adding to said medium approximately 0.04 percent by volume of an iron-dextran complex, inoculating said medium with a culture containing *Neisseria gonorrhoeae*, incubating said bacteria in said medium, and observing the growth of the bacteria after at least about 20 hours.

12. A method for the rapid detection of *Neisseria meningitidis*, comprising providing a meningococcic-specific medium, adding to said medium approximately 0.04 percent by volume of an iron-dextran complex, inoculating said medium with a culture containing *Neisseria meningitidis*, incubating said bacteria in said medium, and observing the growth of the bacteria after at least about 20 hours.

* * * * *

UNITED STATES PATENT OFFICE
CERTIFICATE OF CORRECTION

Patent No. 4,229,530            Dated October 21, 1980

Inventor(s) Richard A. Finkelstein and Shelley M. Payne

It is certified that error appears in the above-identified patent and that said Letters Patent are hereby corrected as shown below:

Col. 1, line 32, rewrite "Public Health Report" as -- Public Health Rep.--;

Col. 3, line 18, before "culture" insert -- solid --;

Col. 4, lines 21-22, rewrite "The samples of Neisseria gonorrhoeae were strain" as -- The samples of Neisseria gonorrhoeae were strain --;

Col. 5, line 51, rewrite "Neisseria meningitidis" as -- Neisseria meningitidis --; and Col. 7, line 35, delete "trails" and insert -- trials --.

Signed and Sealed this

Seventeenth Day of November 1981

[SEAL]

Attest:

GERALD J. MOSSINGHOFF

Attesting Officer     Commissioner of Patents and Trademarks